US012685454B2

(12) United States Patent
Kaczmarek

(10) Patent No.: US 12,685,454 B2
(45) Date of Patent: Jul. 21, 2026

(54) GRAPHICAL REPRESENTATION OF HEMODYNAMIC STATE

(71) Applicant: KONINKLIJKE PHILIPS N.V., Eindhoven (NL)

(72) Inventor: Piotr Kaczmarek, Milton, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 294 days.

(21) Appl. No.: 18/267,804

(22) PCT Filed: Dec. 15, 2021

(86) PCT No.: PCT/EP2021/085811
§ 371 (c)(1),
(2) Date: Jun. 16, 2023

(87) PCT Pub. No.: WO2022/129121
PCT Pub. Date: Jun. 23, 2022

(65) Prior Publication Data
US 2024/0049966 A1 Feb. 15, 2024

Related U.S. Application Data

(60) Provisional application No. 63/126,013, filed on Dec. 16, 2020.

(30) Foreign Application Priority Data

Jan. 11, 2021 (EP) ..................................... 21150858

(51) Int. Cl.
*A61B 5/029* (2006.01)
*A61B 5/00* (2006.01)
(Continued)

(52) U.S. Cl.
CPC .......... *A61B 5/029* (2013.01); *A61B 5/02028* (2013.01); *A61B 5/0205* (2013.01);
(Continued)

(58) Field of Classification Search
None
See application file for complete search history.

(56) References Cited

U.S. PATENT DOCUMENTS 6,409,675 B1 * 6/2002 Turcott ................ A61B 5/0002
600/528
2005/0049511 A1 * 3/2005 Warring-Davies ...........................
A61B 5/02028
600/485

(Continued)

FOREIGN PATENT DOCUMENTS

WO 2009052530 A2 4/2009

OTHER PUBLICATIONS

International Search Report Dated Mar. 18, 2022 For International Appln No. PCT/EP2021/085811 Filed Dec. 15, 2021.
(Continued)

*Primary Examiner* — William L Bashore
*Assistant Examiner* — Koorosh Nehchiri
(74) *Attorney, Agent, or Firm* — Brynne J. Corcoran

(57) ABSTRACT

Methods and apparatus disclosed herein relate to graphical representation of patient hemodynamic state. In various embodiments, one or more measured physiological parameters of a patient may be analyzed. Based on the analysis, a graphical user interface (GUI) may be rendered. The GUI may include a figure-eight schematic (222, 1222) that represents a circulatory system of the patient. The figure-eight schematic may include: a first loop (224, 1224) that represents pulmonary circulation of the patient; a second loop (226, 1226) that represents systemic circulation of the
(Continued)

patient; and a central object (228, 1228) that connects the first and second loops represents a heart of the patient. In various embodiments, each of the first and second loops includes multiple arc fragments, with each arc fragment being shaped to convey one or more of the measured physiological parameters of the patient.

12 Claims, 9 Drawing Sheets

(51) Int. Cl.
    *A61B 5/02*          (2006.01)
    *A61B 5/0205*    (2006.01)
    *A61B 5/021*     (2006.01)
(52) U.S. Cl.
    CPC ............ *A61B 5/021* (2013.01); *A61B 5/4878* (2013.01); *A61B 5/742* (2013.01)

(56)            References Cited

U.S. PATENT DOCUMENTS

| | | | |
|---|---|---|---|
| 2009/0024008 A1 | 1/2009 | Brunner | |
| 2010/0262116 A1* | 10/2010 | Sowb | A61B 5/7445 |
| | | | 604/500 |
| 2011/0087117 A1* | 4/2011 | Tremper | G16H 40/63 |
| | | | 600/595 |
| 2011/0172564 A1* | 7/2011 | Drew | A61B 5/061 |
| | | | 600/587 |
| 2013/0150734 A1 | 6/2013 | Orr | |
| 2013/0324804 A1 | 12/2013 | Mckeown | |
| 2017/0100082 A1* | 4/2017 | Mckeown | A61B 5/0205 |
| 2018/0228386 A1* | 8/2018 | McCall | A61B 5/7445 |
| 2019/0110760 A1* | 4/2019 | Gong | A61B 5/029 |
| 2019/0117070 A1 | 4/2019 | Muhsin | |

OTHER PUBLICATIONS

Michard F (2013) Decision support for hemodynamic management: from graphical displays to closed loop systems. Anesthesia and analgesia 117: 876-882.

Drews FA, Agutter, J. (2001) Evaluating a graphical cardiovascular display for anesthesia. Proceedings of the Human Factors and Ergonomics Society 45th Annual Meeting: 1303-1307.

Agutter J, Drews F, Syroid N, Westneskow D, Albert R, et al. (2003) Evaluation of graphic cardiovascular display in a high-fidelity simulator. Anesthesia and analgesia 97: 1403-1413.

Gurushanthaiah K, Weinger MB, Englund CE (1995) Visual display format affects the ability of anesthesiologists to detect acute physiologic changes. A laboratory study employing a clinical display simulator. Anesthesiology 83: 1184-1193.

Charabati S, Bracco D, Mathieu PA, Hemmerling TM (2009) Comparison of four different display designs of a novel anaesthetic monitoring system, the 'integrated monitor of anaesthesia (IMA)'. British journal of anaesthesia 103: 670-677.

Koch SH, Weir C, Haar M, Staggers N, Agutter J, et al. (2012) Intensive care unit nurses' information needs and recommendations for integrated displays to improve nurses' situation awareness. Journal of the American Medical Informatics Association: JAMIA 19: 583-590.

Michard F, Gan TJ, Kehlet H (2017) Digital innovations and emerging technologies for enhanced recovery programmes. British journal of anaesthesia 119: 31-39.

Gorges M, Staggers N (2008) Evaluations of physiological monitoring displays: a systematic review. Journal of clinical monitoring and computing 22: 45-66.

Blike GT, Surgenor SD, Whalen K, Jensen J (2000) Specific elements of a new hemodynamics display improves the performance of anesthesiologists. Journal of clinical monitoring and computing 16: 485-491.

Wachter SB, Agutter J, Syroid N, Drews F, Weinger MB, et al. (2003) The employment of an iterative design process to develop a pulmonary graphical display. Journal of the American Medical Informatics Association: JAMIA 10: 363-372.

Sanderson PM, Watson MO, Russell WJ (2005) Advanced patient monitoring displays: tools for continuous informing. Anesthesia and analgesia 101: 161-168, table of contents.

Kamaleswaran R, McGregor C (2016) A Review of Visual Representations of Physiologic Data. JMIR medical informatics 4: e31.

Michard F, Gan, T.J., Bellomo, R. (2019) Protecting ward patients: the case for continuous monitoring. ICU Management & Practice Intensive care—Emergency Medicine—Anaesthesiology 19: 60-62.

Ehrenfeld JM, Henneman, J.P., Bulka, C.M., Sandberg, W.S. (2014) Continuous Non-invasive Hemoglobin Monitoring during Orthopedic Surgery: A Randomized Trial. J Blood Disorders Transf 5: 237-241.

Maheshwari K, Shimada T, Fang J, Ince I, Mascha EJ, et al. (2019) Hypotension Prediction Index software for management of hypotension during moderate- to high-risk noncardiac surgery: protocol for a randomized trial. Trials 20: 255.

Pearse RM, Ikram K, Barry J (2004) Equipment review: an appraisal of the LiDCO plus method of measuring cardiac output. Critical care 8: 190-195.

EV 1000 Clinical Platform Brochure, p. 5.

* cited by examiner

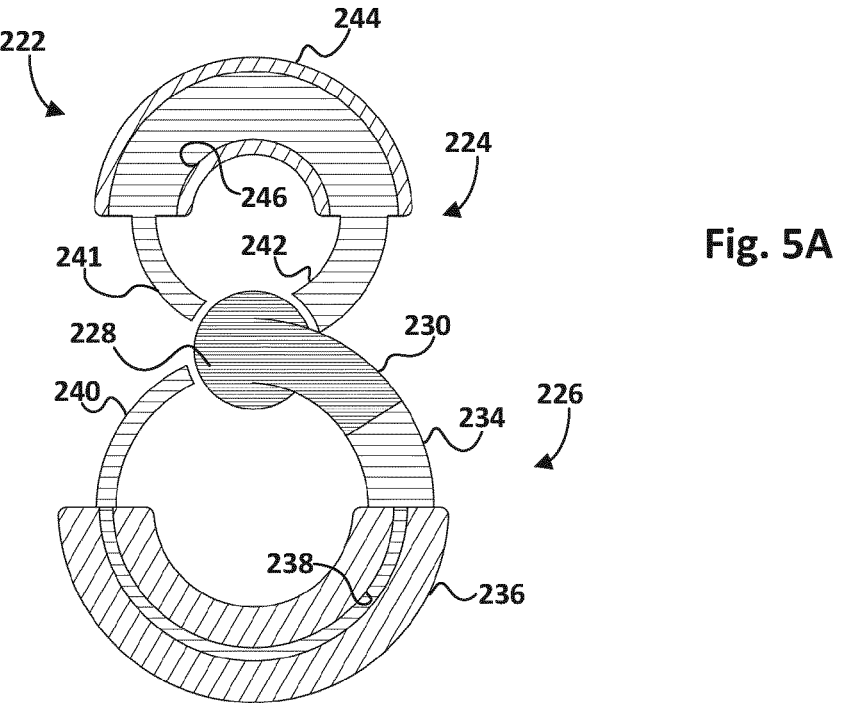
Fig. 5A
Fig. 5B
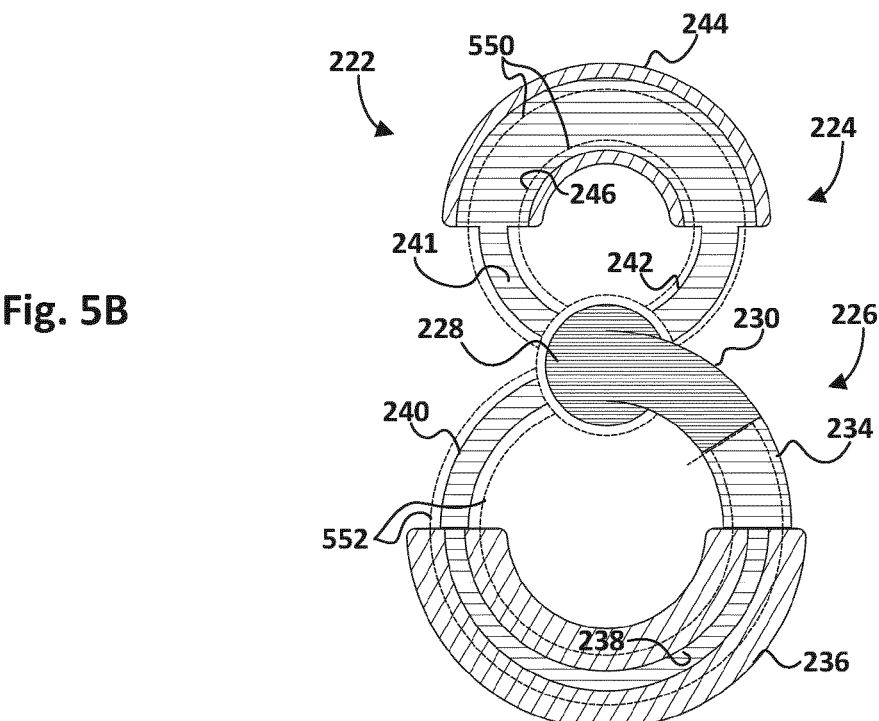

1300

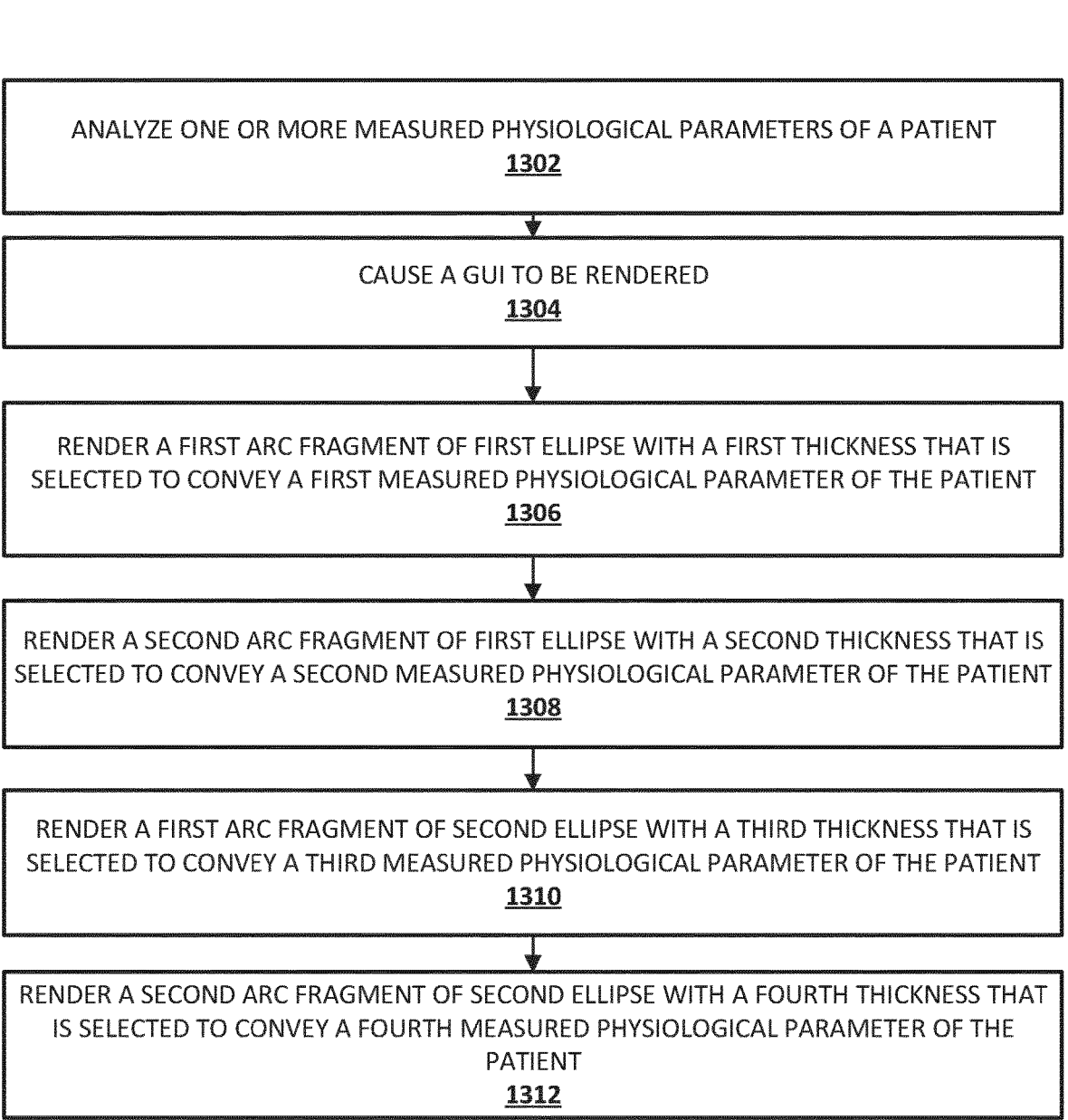

ANALYZE ONE OR MORE MEASURED PHYSIOLOGICAL PARAMETERS OF A PATIENT
1302

CAUSE A GUI TO BE RENDERED
1304

RENDER A FIRST ARC FRAGMENT OF FIRST ELLIPSE WITH A FIRST THICKNESS THAT IS SELECTED TO CONVEY A FIRST MEASURED PHYSIOLOGICAL PARAMETER OF THE PATIENT
1306

RENDER A SECOND ARC FRAGMENT OF FIRST ELLIPSE WITH A SECOND THICKNESS THAT IS SELECTED TO CONVEY A SECOND MEASURED PHYSIOLOGICAL PARAMETER OF THE PATIENT
1308

RENDER A FIRST ARC FRAGMENT OF SECOND ELLIPSE WITH A THIRD THICKNESS THAT IS SELECTED TO CONVEY A THIRD MEASURED PHYSIOLOGICAL PARAMETER OF THE PATIENT
1310

RENDER A SECOND ARC FRAGMENT OF SECOND ELLIPSE WITH A FOURTH THICKNESS THAT IS SELECTED TO CONVEY A FOURTH MEASURED PHYSIOLOGICAL PARAMETER OF THE PATIENT
1312

Fig. 13

GRAPHICAL REPRESENTATION OF HEMODYNAMIC STATE

CROSS-REFERENCE TO PRIOR APPLICATIONS

This application is the U.S. National Phase application under 35 U.S.C. § 371 of International Application No. PCT/EP2021/085811, filed on Dec. 15, 2021, which claims the benefit of European Application No. 21150858.5 filed on Jan. 11, 2021 and U.S. Provisional Application No. 63/126, 013 filed Dec. 16, 2020. These applications are hereby incorporated by reference herein.

TECHNICAL FIELD

Various embodiments described herein are directed generally to health care. More particularly, but not exclusively, various methods and apparatus disclosed herein relate to graphical representation of a condition of the patient's circulatory system.

BACKGROUND

Large numbers of physiological parameters may be measured for a patient, especially if they are in a heightened state of monitoring, such as being in an intensive care unit (ICU). Presenting these measured physiological parameters to health care personnel such as doctors and nurses can be challenging. Presenting too many measured physiological parameters can be overwhelming, while presenting too few may not sufficiently inform the health care personnel of a condition of the patient's circulatory system, particularly a change in the condition.

In the patient monitoring context, many existing patient monitors are devoted to representing numerical displays and waveforms as part of a graphical user interface (GUI). However, existing circulatory system GUIs suffer from various issues. Existing circulatory GUIs fail to keep up with the proliferation of new, non-invasive technologies providing increasing numbers of reliable hemodynamic measurements. Some offer too much detail and/or are too complex, straining a clinician's cognitive abilities. Others may offer too little detail, which may cause changes in the patient's hemodynamic state to go unnoticed. Some circulatory system displays employ gratuitous naturalistic representation of a patient's organs, which is unnecessary for experienced clinicians and is often employed as an illustrative, if somewhat uninformative, backdrop for relatively sparse numerical data.

US 2019/110760 A1 discloses a method for dynamically displaying a change of a parameter measured at an interval. The method comprises: dynamically monitoring at least one type of hemodynamic parameters of a patient by means of a sensor on a monitor; obtaining a first monitoring value of the type of hemodynamic parameters monitored at a first monitoring time; displaying a first form corresponding to the first monitoring value in a simulated graph corresponding to each type of the hemodynamic parameters on a graphic display interface; obtaining a second monitoring value of the type of hemodynamic parameters monitored at a second monitoring time, and determining a second form of the corresponding simulated graph; and adjusting the simulated graph corresponding to each type of hemodynamic parameter from the first form to the second form on the graphic display interface. Also provided are a corresponding system and a dynamic monitor.

US 2017/100082 A1 discloses a patient monitoring and display system. The system allows a clinician to trigger the occurrence of a clinical event, and record a patient's status following the clinical event. The system calculates and displays a change in a patient's status resulting from the clinical event. The system allows multiple parameters to be tracked and displayed on a single screen. The system can also display various animated organs, such as a heart or a lung, corresponding to an operation of the organs in the patient.

SUMMARY

The present disclosure is directed to methods and apparatus for graphical representation of the state of circulatory systems of patients. For example, in various embodiments, a GUI that is rendered on a display may include one or more graphical elements that convey, in a manner that is intuitive and quickly-digestible, various measured physiological parameters associated with a patient's hemodynamic state and the relationships between those parameters. In various embodiments, these graphical elements may have various spatial dimensions that are selected to convey measured physiological parameters associated with the state of circulatory system.

For example, a GUI configured with selected aspects of the present disclosure may include a figure-eight schematic that represents a circulatory system of the patient. A first loop of the figure-eight schematic may represent pulmonary circulation of the patient. A second loop of the figure-eight schematic, which in some embodiments may be presented underneath the first loop, may represent systemic circulation of the patient. A central rounded object that connects the first and second loops may represent a heart of the patient, and in some embodiments may be shaped to convey end diastolic volume (EDV) of the patient. In some embodiments, one or both of the first and second loops may include multiple arc fragments. Each arc fragment may be shaped to convey one or more of the measured physiological parameters of the patient. As used herein, the verb "shape" in its various forms refers to selecting any spatial dimension of a graphical element, in isolation and/or relative to other aspects of the graphical element, including a size of any part of the graphical element. Thus, for instance, various arc fragments can have relative widths or thicknesses that convey various medical conditions depending on which arc fragments are thicker and which are thinner.

Embodiments described herein give rise to various technical advantages. The figure-eight schematics allow medical personnel to easily ascertain/understand/intuit a patient's circulatory state, without having to consult electronic medical records (EMRs) and/or patient data management systems (PDMSs). Moreover, in embodiments where components of the figure-eight schematics are given relative thicknesses, a clinician can quickly ascertain where problems may be originating and/or what other areas those problems may affect. For example, normalizing different measured physiological parameters in order that they be conveyed or "encoded" into various points of one or more continuous shapes (e.g., the figure-eight schematic) may provide clinician's with a clear idea of what's "normal" or "baseline," and how a particular patient's measured physiological parameters diverge from normal/baseline. Moreover, given their compact nature, it is possible to render figure-eight schematics in a small area, such as a smart watch display, a patient monitor (which typically have small displays), and/or a small region of a nurse station's monitor (to allow information for other patients to also be displayed at the same time), and yet a large amount of information is still conveyed. In some implementations, figure-eight schematics may even be rendered in a paper or electronic document, such as an EMR, as a snapshot of the patient's circulatory system.

Generally, in one aspect, a method may be implemented using one or more processors, and may include: analyzing one or more measured physiological parameters of a patient; based on the analyzing, causing a graphical user interface to be rendered, wherein the graphical user interface includes a figure-eight schematic that represents a circulatory system of the patient, wherein: a first loop of the figure-eight schematic represents pulmonary circulation of the patient; a second loop of the figure-eight schematic represents systemic circulation of the patient; a central object that connects the first and second loops represents a heart of the patient and is shaped to convey an end diastolic volume (EDV) of the patient, and each of the first and second loops includes multiple arc fragments, with each arc fragment being shaped to convey one or more of the measured physiological parameters of the patient, wherein cardiac output of the patient is conveyed by a length of an arc fragment of the second loop that extends from the central rounded object.

In various embodiments, the method may include: rendering a first arc fragment of the first loop with a first thickness that is selected to convey a mean pulmonary arterial pressure (MPAP) of the pulmonary circulation of the patient; rendering a second arc fragment of the first loop with a second thickness that is selected to convey pulmonary artery occlusion pressure (PAOP) of the pulmonary circulation of the patient; rendering a first arc fragment of the second loop with a third thickness that is selected to convey a mean arterial pressure (MAP) of the systemic circulation of the patient; and/or rendering a second arc fragment of the second loop with a fourth thickness that is selected to convey central venous pressure (CVP) of the systemic circulation of the patient.

In various embodiments, a stroke volume of the patient may be conveyed by a length of a secondary arc-shaped element that extends from within the arc fragment of the second loop.

In various embodiments, the method may include rendering an arc-shaped envelope with an arc-shaped channel, wherein a bore of the arc-shaped channel is sized to convey vascular resistance by constricting a thickness of a portion of the first or second loop. In various embodiments, one or more of the multiple arc fragments may include visual annotations of normal or baseline ranges of the respective one or more of the measured physiological parameters of the patient.

In various embodiments, at least a portion of the first loop may be superimposed over a rendered pair of lungs. In various embodiments, the method may include animating the pair of lungs to demonstrate breathing of the patient. In various embodiments, the method may include rendering the pair of lungs with a visual annotation that represents a level of extravascular lung water (EVLW) of the patient.

In addition, some implementations include one or more processors of one or more computing devices, where the one or more processors are operable to execute instructions stored in associated memory, and where the instructions are configured to cause performance of any of the aforementioned methods. Some implementations also include one or more non-transitory computer readable storage media storing computer instructions executable by one or more processors to perform any of the aforementioned methods.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating various principles of the embodiments described herein.

FIGS. 5A and 5B depict more example figure-eight schematics configured with selected aspects of the present disclosure.

FIG. 13 depicts an example method for practicing selected aspects of the present disclosure.

DETAILED DESCRIPTION

Large numbers of physiological parameters may be measured for a patient, especially if they are in a heightened state of monitoring, such as being in an intensive care unit (ICU). Mental processing of these measured physiological parameters by health care personnel such as doctors and nurses can strain their cognitive abilities. For example, the circulatory information presented by many existing circulatory displays may not be effective in demonstrating how various measured physiological parameters associated with a state of the patient's circulatory system interact with each other. In view of the foregoing, various embodiments and implementations of the present disclosure are directed to improved graphical representation of a state of the patient's circulatory system.

Figure 1:
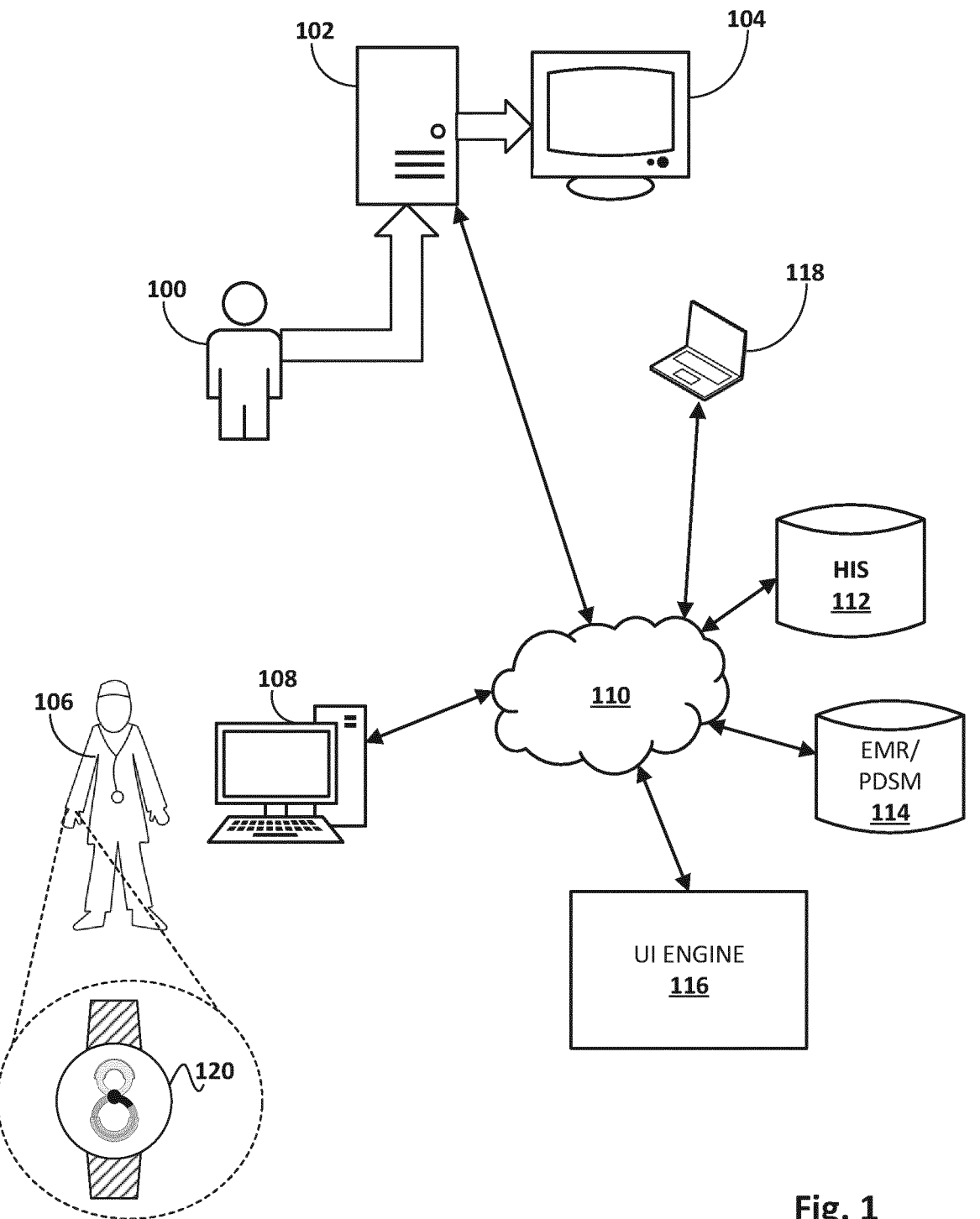
FIG. 1 illustrates an example environment in which selected aspects of the present disclosure may be practiced.

FIG. 1 depicts an example environment with various components that may practice selected aspects of the present disclosure. A patient 100 may have various physiological parameters measured, e.g., by various types of probes, electrodes, laboratory tests, swabs, etc. One or more of those measured physiological parameters may be provided to a local computing device 102 that is operably coupled with a patient monitor 104. In some embodiments, patient monitor 104 may be a standalone computing device with onboard logic such as processor(s) and memory, in which case computing device 102 may be omitted. Patient monitor 104 may display a graphical user interface ("GUI", not depicted in FIG. 1) that is configured with selected aspects of the present disclosure to convey information about a circulatory system of patient 100.

Health care personnel 106 such as doctors, nurses, clinicians, etc., may read patient monitor 104 directly, and/or may operate various types of client computing devices 108 to view GUIs rendered with selected aspects of the present disclosure. Computing device 108 (or other computing devices mentioned herein) may take various forms, such as one or more of: a desktop computing device, a laptop computing device, a tablet computing device, a mobile phone computing device, a computing device of a vehicle of the user (e.g., an in-vehicle communications system, an in-vehicle entertainment system, an in-vehicle navigation system), a standalone interactive speaker (which in some cases may include a vision sensor), a smart appliance such as a smart television (or a standard television equipped with a networked dongle with automated assistant capabilities), and/or a wearable apparatus of the user that includes a computing device (e.g., a watch of the user having a computing device, glasses of the user having a computing device, a virtual or augmented reality computing device). Additional and/or alternative client computing devices may be provided.

Various components depicted in FIG. 1, such as computing device 102, computing device 108, and/or patient monitor 104, may be in network communication with each other over one or more computer networks 110. One or more computer networks 110 may include wired and/or wireless local area and/or wide area networks (e.g., the Internet). Various computer networking technologies may be implemented to facilitate communication between the various components, such as Wi-Fi, cellular, Ethernet, fiber optic, etc.

Various information systems may be provided that are accessible to obtain various data points relevant to the present disclosure. For example, a hospital information system (HIS) 112 and/or an EMR/PDMS system 114 may receive and/or maintain, e.g., as part of EMRs for patients, measured physiological parameters. A user interface (UI) engine 116 may be configured to practice selected aspects of the present disclosure in order to cause various display devices, such as patient monitor 104, computing device 108, or other devices such as a laptop computer 118 controlled by patient 100 (e.g., in their home, or in their relative's home) and/or smart watch 120 worn by health care personnel 106 (or by a patient), to render GUIs configured with selected aspects of the present disclosure.

In some implementations, UI engine 116 may distribute data in various forms to cause GUIs configured with selected aspects of the present disclosure to be rendered on remote computing devices. In some implementations, UI engine 116 may distribute markup language documents (e.g., HTML, XML) that are rendered by web browsers or other applications. In some embodiments, UI engine 116 may distribute graphics data that is usable at remote computing devices to render figure-eight schematics configured with selected aspects of the present disclosure. In various implementations, these graphics data may take the form of vector graphics, rasterized/bitmap graphics, etc. In other implementations, UI engine 116 may be implemented in whole or in part on a client device, e.g., based on data received at the client device from UI engine 116.

In some implementations, UI engine 116 may obtain measured physiological parameters from other information systems (e.g., 112, 114), from laboratories, and/or from equipment being used to monitor physiological parameter(s) of patient 100, normalize and analyze these data points, and based on the analysis, render graphical elements that convey various aspects of the circulatory system of patient 100. While depicted separately from HIS 112 and EMR/PDMS 114 in FIG. 1, in other embodiments, UI engine 116 may be integral with either of these other information systems. In some embodiments, a patient may also wear a smart watch and/or wearable patient monitor (not depicted) that includes a display on which GUIs configured with aspects of the present disclosure may be rendered.

Figures 2A, 2B:
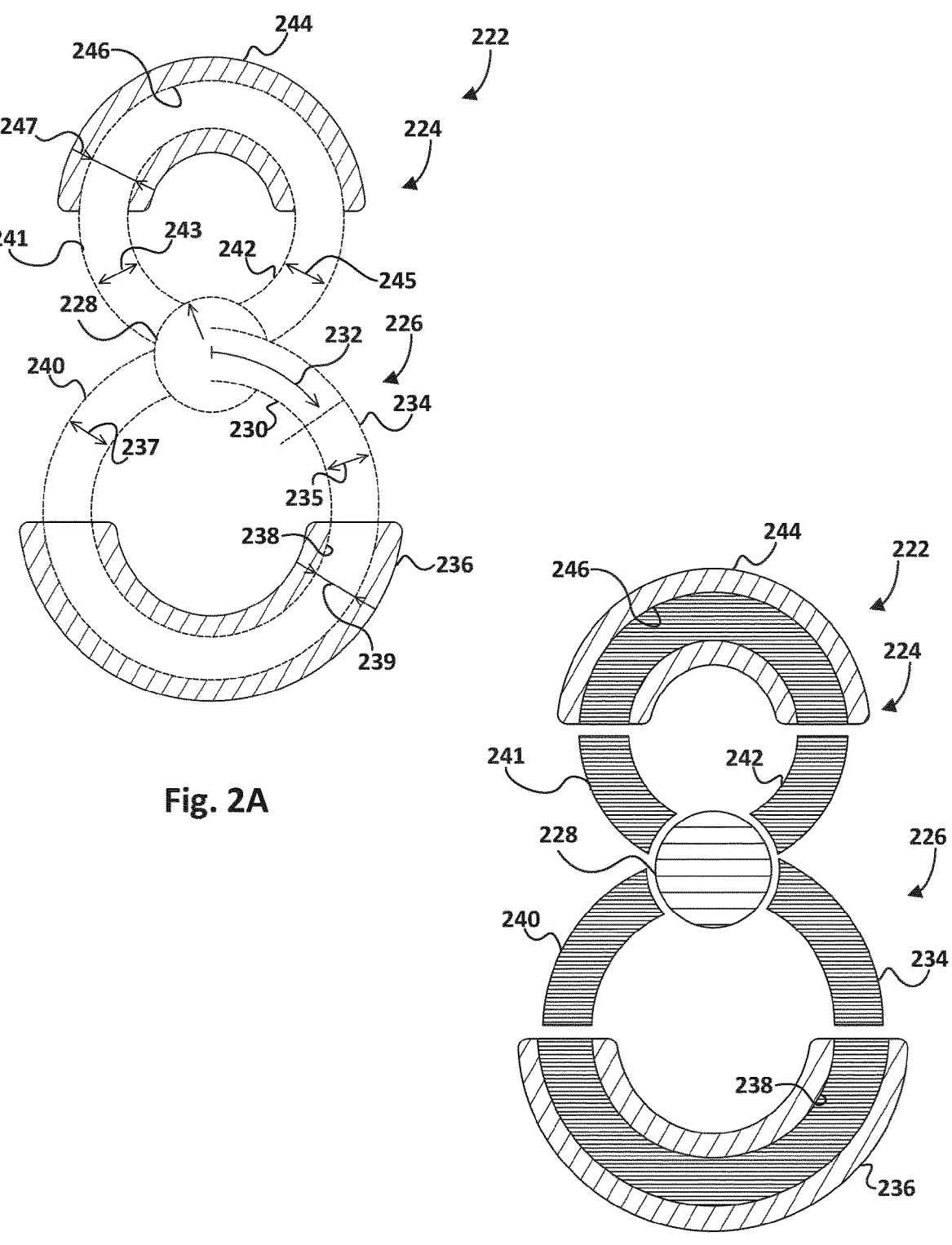
FIGS. 2A-B depict examples of a figure-eight schematic without any encoded physiological measurements, in accordance with selected aspects of the present disclosure.

FIGS. 2A and 2B depict an example figure-eight schematic 222 that may be rendered as part of a GUI, in accordance with various embodiments. FIG. 2A includes a number of visual annotations in the form of arrows that demonstrate how various portions can be shaped to convey various physiological information about patient 100. FIG. 2B depicts in greater detail how figure-eight schematic may be divided logically into a plurality of arc fragments, each corresponding to a different measured physiological parameter of patient 100.

Referring to both FIGS. 2A and 2B, figure-eight schematic 222 includes a first loop 224 (which may be a perfect circle, an oval shape, or some other circuitous shape, for instance) that represents aspects of pulmonary circulation of patient 100. Figure-eight schematic 222 also includes a second loop 226 (which may be a perfect circle or an oval shape, for instance) that represents aspects of systemic circulation of patient 100. In other words, top loop 224 represents circulation in the lungs of patient 100 and bottom loop 226 represents circulation elsewhere in patient 100. Just as the lungs and the rest of a circulation system are connected by the heart, figure-eight schematic also includes a central object 228 (which may be a perfect circle or an oval shape, for instance) that represents a heart of patient 100.

In various embodiments, one or both of the first loop 224 and second loop 226 may include (e.g., be logically divided into) multiple arc fragments. This is best seen in FIG. 2B, although the fragments are also labeled in FIG. 2A. Each arc fragment may be shaped to convey one or more measured physiological parameters of patient 100, and more particularly, various pressures and/or resistances measured within patient 100. Various arrows are provided in FIG. 2A to demonstrate one example of how these various physiological parameters may be conveyed. In order that different measured physiological parameters having different values can be viewed together on a single figure-eight schematic, in various implementations, one or more measured physiological values may be normalized with respect to other measured physiological value(s). This allows for relative thicknesses of arc fragments to effectively convey a patient's hemodynamic state in an intuitive and informative manner.

In some implementations, central object 228 is shaped (e.g., sized) to convey an end diastolic volume (EDV) of patient 100. Cardiac output of the patient may be conveyed in some embodiments by an arc length 232 of an arc fragment 230 (referred to as "CO arc fragment" herein) of second loop 226 that extends from central object 228. Although not depicted in FIGS. 2A-B, in some embodiments, a stroke volume of patient 100 may be conveyed by a length of a secondary arc-shaped element that extends from within CO arc fragment 230 (see 352 in FIG. 4).

Just downstream from CO arc fragment 230 is a mean arterial pressure (MAP) arc fragment 234. MAP arc fragment 234 may have a thickness (indicated by the double-headed arrow 235) that is selected based on a MAP measure of patient 100. As an example, for a patient with high blood pressure, MAP arc fragment 234 may be relatively thick. For a patient with low blood pressure, MAP arc fragment 234 may be relatively thin. The thickness of CO arc fragment 230 conforms to (e.g., may be the same as) the MAP encoding arc 234.

Rendered just downstream from MAP arc fragment 234 is an arc-shaped envelope 236 with an arc-shaped channel 238. Arc-shaped channel 238 may be bored or have a bore that is sized to convey systematic vascular resistance (SVR) by constricting a thickness of a portion of second loop 226, as shown by the inwardly-pointing arrows 239 at bottom right in FIG. 2A. As an example, for a patient with high SVR arc fragment 238 may be relatively thin. For a patient with low SVR arc fragment 238 may be relatively thick.

Downstream from arc-shaped envelop 236, a central venous pressure (CVP) arc fragment 240 may be shaped to convey a CVP measurement of patient 100, which also may a reasonable approximation of right atrial pressure (RAP) and/or as a surrogate for preload. After CVP arc fragment 240, flow returns to central object 228, which as noted above corresponds to the heart of patient 100. Thus, for instance, a thickness of CVP arc fragment 240 may represent a pressure of venous blood returning to the heart of patient 100.

Attention will now turn to first loop 224 representing pulmonary circulation of patient 100. A mean pulmonary arterial pressure (MPAP) arc fragment 241 may be shaped to have a width (conveyed by the double-headed arrow 243) that conveys a MPAP of patient 100. Similarly, a pulmonary artery wedge pressure (PAWP) or pulmonary artery occlusion pressure (PAOP) arc fragment 242 may be shaped to have a width (conveyed by the double-headed arrow 245) that conveys a PAWP/PAOP measurement of patient 100.

Similar to arc-shaped envelope 236 in second loop 226 (systemic circulation) of patient 100, another arc-shaped envelope 244 with an arc-shaped channel 246 may be provided between MPAP arc fragment 241 and PAWP arc fragment 242. Arc-shaped channel 246 may be bored or have a bore that is sized over a portion of first loop 224 to convey pulmonary vascular resistance (PVR) by constricting its thickness, as shown by the inwardly-pointing arrows 247 at top left in FIG. 2A. As an example, for a patient with high PVR arc fragment 246 may be relatively thin.

In FIGS. 2A-B, figure-eight schematic 222 was depicted without underlying physiological measurements. Various additional figures that will now be discussed demonstrate how figure-eight schematic 222 may appear under a variety of circumstances. Starting at FIG. 3, figure-eight schematic 222 is rendered with CO arc fragment 230 of second loop 226 extending from central object 228 by an arc length 232 that conveys cardiac output (CO) of patient 100. In some embodiments, and as is depicted in FIG. 4, a stroke volume (SV) of patient 100 may be conveyed by a length of a secondary arc-shaped element 352 that extends from within CO arc fragment 230.

Figure 3:
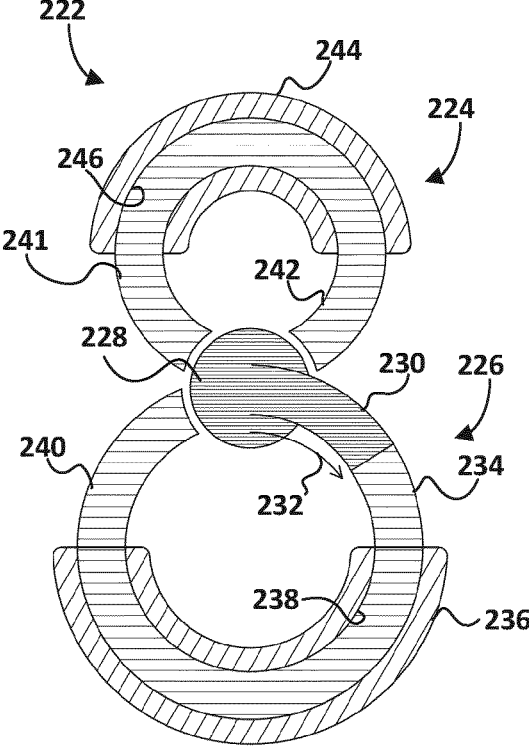
FIGS. 3 and 4 demonstrate an example of how end diastolic volume, stroke volume, and cardiac output may be conveyed, in accordance with various embodiments.
Figure 4:
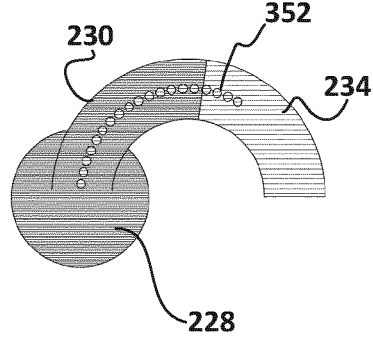

The thicknesses of the arc fragments in FIG. 3 are relatively uniform, suggesting that the patient's physiological measurements are within normal ranges. FIG. 3 therefore demonstrates a possible goal of the normalization mentioned previously—to ensure that for a patient with measured physiological parameters in normal ranges, thicknesses of the various arc fragments are more or less uniform. Although not depicted in the Figures, in some implementations, the various arc fragments may be further visually annotated to convey what they represent. For instance, MPAP arc fragment 241 may be labeled "MPAP," and may or may not also be labeled with a numerical value. Other arc fragments may or may not be annotated similarly.

FIGS. 5A and 5B depict variations of figure-eight schematic 222 without and with visual annotations showing normal or baseline values. In both FIGS. 5A and 5B, pulmonary circulation of patient 100 is demonstrated by first loop 224 as having low pressure and low resistance. For example, arc-shaped channel 246 is expanded or dilated. By contrast, systemic circulation of patient 100 is demonstrated by second loop 226 has having high pressure and high resistance, while preload (EDV) is close to normal. For example, arc-shaped channel 238 is constricted. In FIG. 5B, visual annotations in the form of lines 550, 552 are shown on top of the underlying arc fragments to demonstrate to the clinician how the various measured physiological parameters compare to normal or baseline measures. These visual annotations are absent in FIG. 5A.

Figures 6, 7, 8, 9:
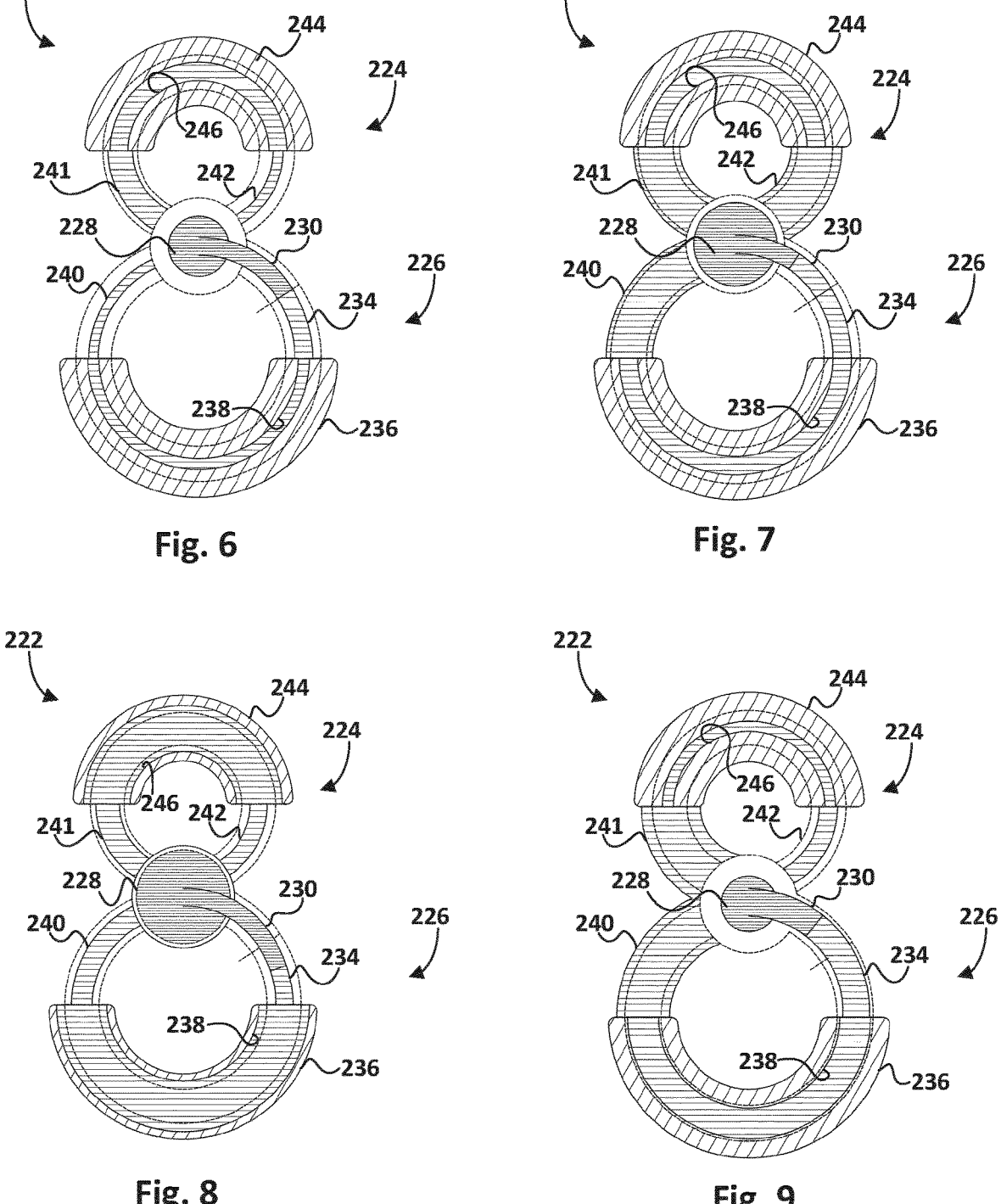
FIGS. 6, 7, 8, and 9 depict examples of how figure-eight schematics may appear under a variety of health circumstances, in accordance with selected aspects of the present disclosure.

FIGS. 6-9 depict examples of how figure-eight schematic 222 may appear under a variety of health circumstances, in accordance with selected aspects of the present disclosure. In FIG. 6, patient 100 is undergoing hypovolemic shock, a life-threatening condition that results when patient 100 loses more than some percentage (e.g., 20%) of his or her blood supply. Consequently, PAOP arc fragment 242, MAP arc fragment 234, CVP arc fragment 240, and MPAP arc fragment 241 are each rendered narrowly to convey their respective low pressures. Arc-shaped channel 246 of arc-shaped envelope 244 and arc-shaped channel 238 of arc-shaped envelope 236 are rendered in constricted configurations to demonstrate high PVR and SVR, respectively.

In FIG. 7, patient 100 is undergoing cardiogenic shock, a life-threatening condition that results when the patient's heart cannot pump sufficient oxygen to organs such as the brain and kidneys. One common cause of cardiogenic shock is a heart attack. In FIG. 7, PAOP arc fragment 242, CVP arc fragment 240, and MPAP arc fragment 241 are each rendered with relatively wide thicknesses to convey their respective high pressures. By contrast, MAP arc fragment 234 is rendered relatively narrowly to demonstrate a relatively low pressure. Arc-shaped channel 246 of arc-shaped envelope 244 and arc-shaped channel 238 of arc-shaped envelope 236 are once again rendered in constricted configurations to demonstrate high PVR and SVR, respectively. A suitably-trained clinician can view the configuration depicted in FIG. 7 to quickly conclude that patient 100 is undergoing cardiogenic shock.

In FIG. 8, patient 100 is undergoing septic shock, a life-threatening condition that results when a patient's blood pressure drops to dangerously low levels after infection, mostly but not exclusively caused by bacteria. Consequently, PAOP arc fragment 242, MAP arc fragment 234, CVP arc fragment 240, and MPAP arc fragment 241 are each rendered narrowly to convey their respective low pressures. Arc-shaped channel 246 of arc-shaped envelope 244 and arc-shaped channel 238 of arc-shaped envelope 236 are rendered in un-constricted or dilated configurations to demonstrate low PVR and SVR, respectively. A suitably-trained clinician can view the configuration depicted in FIG. 8 to quickly conclude that patient 100 is undergoing septic shock.

In FIG. 9, patient 100 is undergoing a pulmonary embolism, or a blockage in one of the pulmonary arteries in the lungs of patient 100. Consequently, PAOP arc fragment 242 and MAP arc fragment 234 are each rendered narrowly to convey their respective low pressures. By contrast, CVP arc fragment 240 and MPAP arc fragment 241 are rendered relatively thickly to convey their respective high pressures. Arc-shaped channel 246 of arc-shaped envelope 244 is rendered in a constricted configuration to demonstrate high PVR. By contrast, arc-shaped channel 238 of arc-shaped envelope 236 is rendered un-constricted or dilated to demonstrate normal SVR. A suitably-trained clinician can view the configuration depicted in FIG. 9 to quickly conclude that patient 100 has experienced a pulmonary embolism.

Figures 10, 11:
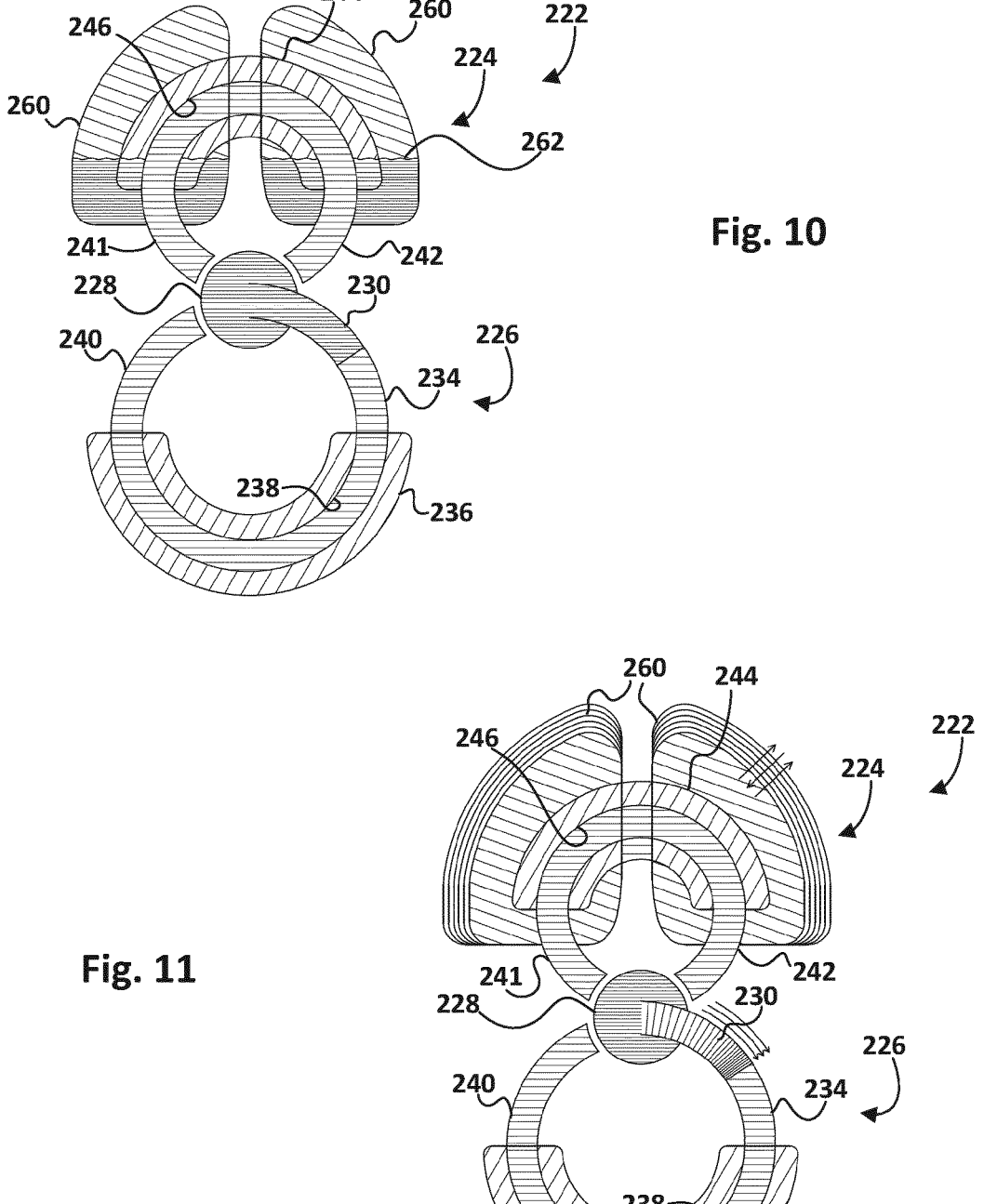
FIGS. 10 and 11 depict variations of the figure-eight schematic, in accordance with selected aspects of the present disclosure.

FIGS. 10 and 11 depict variations of the figure-eight schematic, in accordance with selected aspects of the present disclosure. In each figure, a portion of first loop 224 is superimposed over a rendered pair of lungs 260. Pair of lungs 260 may be visually annotated and/or rendered in various ways to convey various information. In FIG. 10, for instance, pair of lungs 260 includes a schematic rendition of a fluid 262 that rises within pair of lungs 260 to convey an extravascular lung water (EVLW) or extravascular lung water index (ELWI).

In FIG. 11, pair of lungs 260 is animated to demonstrate breathing of the patient. For example, pair of lungs 260 may be animated to expand upon the patient inhaling and contract upon the patient exhaling. Another animation may also inform the user of aortic blood movement that in turn aids in recognition of abnormalities, e.g., by showing CO arc fragment 230 extend and retract in synchronization with pulse rate.

In some embodiments, figure-eight schematic 222 may be animated to depict changes in a patient's hemodynamic state over time. For example, the thicknesses of the various arc fragments may be altered over time to demonstrate the patient's ongoing hemodynamic state. Should the patient be afflicted with a condition, such as any of those depicted in FIGS. 6-9, this change may be evident in these animations, and can be used as part of clinical decision support (CDS) analysis. In some such embodiments, a clinician may be able to scroll through a timeline to "fast forward" and/or "rewind" these animations to determine, for instance, how a particular condition developed and/or to obtain a holistic overview of the patient's hemodynamic state at various points in time.

Figure 12:
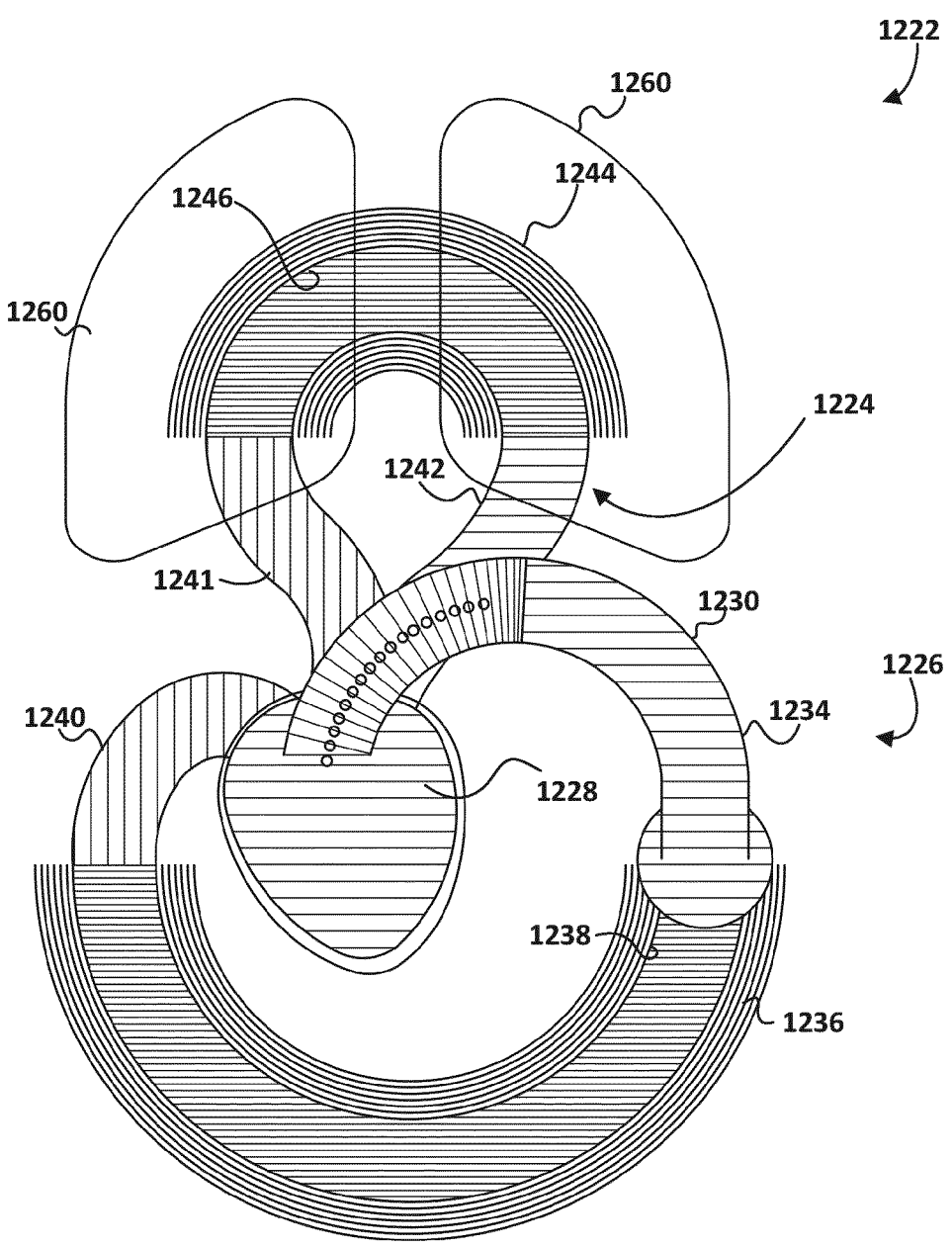
FIG. 12 depicts an alternative figure-eight schematic configured with selected aspects of the present disclosure.

Figure-eight schematics are not limited to the mostly circular loops depicted in previous figures. In various embodiments, figure-eight schematics may include loops have different shapes. FIG. 12 depicts an example figure-eight schematic 1222 with components that are labeled similarly to components in other figures, except that the reference numbers begin with "12" rather than "2." A first loop 1224 has a mostly circular shape but its interface with a central object 1228 is different than depicted in previous figures.

In addition, in FIG. 12, central object 1228 is shaped differently than central object 228 in previous figures, with central object 1228 being vaguely heart-shaped. Further, in FIG. 12, second loop 1226 has a shape that is somewhat circular, but like first loop 1224, the interface between second loop 1226 and central object 1228 is different than the interface between second loop 226 and central object 228 in previous figures.

Referring now to FIG. 13, an example method 1300 of practicing selected aspects of the present disclosure is described. For convenience, the operations of the flowchart are described with reference to a system that performs the operations. This system may include various components of various computer systems. For instance, various operations may be performed by one or more components of UI engine 116 or other components of FIG. 1. Moreover, while operations of method 1300 are shown in a particular order, this is not meant to be limiting. One or more operations may be reordered, omitted or added.

At block 1302, the system may analyze one or more measured physiological parameters of a patient, especially parameters related to the patient's circulatory system, such as PVR, MPAP, EDV, CVP, PAOP, CO, SV, MAP, and/or SVR. Based on the analyzing, at block 1304, the system may cause a GUI to be rendered. In various implementations, the GUI may include a figure-eight schematic (e.g., 222) that represents the patient's circulatory system. For example, and as shown in previous figures, figure-eight schematic 222 may include: a first loop 224 that represents pulmonary circulation of the patient; a second loop 226 that represents systemic circulation of the patient; and a central rounded object 228 that connects the first and second loops and represents a heart of the patient. In some embodiments, central rounded object 228 may be shaped (e.g., have a diameter that is selected) to convey an EDV of the patient.

In various embodiments, one or both of the first and second loops may include multiple arc fragments. Each arc fragment may be shaped to convey a respective measured physiological parameter of the patient. For example, at block 1306, the system may render a first arc fragment 241 of first loop 224 with a first thickness that is selected to convey a first measured physiological parameter of patient 100, such as an MPAP of patient 100. At block 1308, the system may render a second arc fragment 242 of first loop 224 with a second thickness that is selected to convey a second measured physiological parameter of patient 100, such as a PAOP of the patient.

As additional examples, at block 1310, the system may render a first arc fragment 234 of second loop 226 with a third thickness that is selected to convey a third measured physiological parameter of patient 100, such as a MAP of patient 100. At block 1312, the system may render a second arc fragment 240 of second loop 226 with a fourth thickness that is selected to convey a fourth measured physiological parameter of patient 100, such as CVP of the patient.

Figure 14:
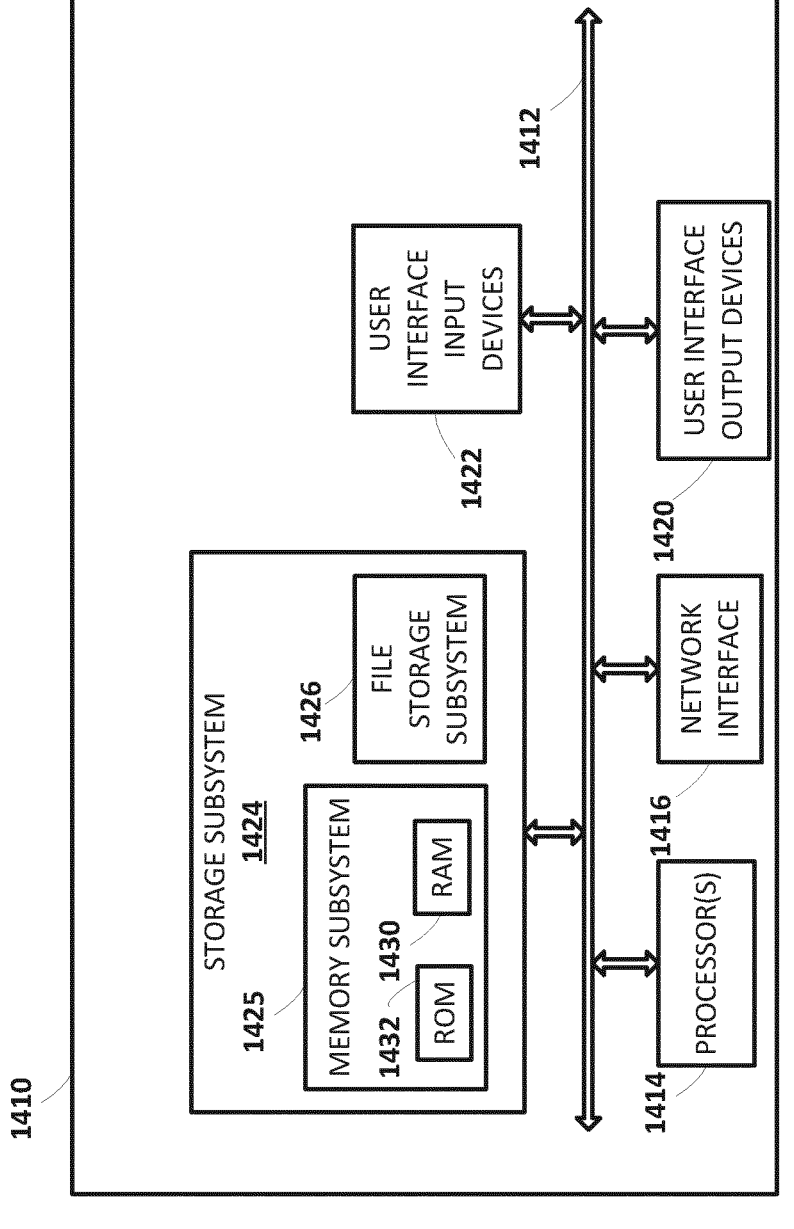
FIG. 14 depicts an example computing system architecture.

FIG. 14 is a block diagram of an example computing device 1410 that may optionally be utilized to perform one or more aspects of techniques described herein. Computing device 1410 typically includes at least one processor 1414 which communicates with a number of peripheral devices via bus subsystem 1412. These peripheral devices may include a storage subsystem 1424, including, for example, a memory subsystem 1425 and a file storage subsystem 1426, user interface output devices 1420, user interface input devices 1422, and a network interface subsystem 1416. The input and output devices allow user interaction with computing device 1410. Network interface subsystem 1416 provides an interface to outside networks and is coupled to corresponding interface devices in other computing devices.

User interface input devices 1422 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computing device 1410 or onto a communication network.

User interface output devices 1420 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computing device 1410 to the user or to another machine or computing device.

Storage subsystem 1424 stores programming and data constructs that provide the functionality of some or all of the modules described herein. For example, the storage subsystem 1424 may include the logic to perform selected aspects of the method of FIG. 13, as well as to implement various components depicted in FIG. 1.

These software modules are generally executed by processor 1414 alone or in combination with other processors. Memory 1425 used in the storage subsystem 1424 can include a number of memories including a main random access memory (RAM) 1430 for storage of instructions and data during program execution and a read only memory (ROM) 1432 in which fixed instructions are stored. A file storage subsystem 1426 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 1426 in the storage subsystem 1424, or in other machines accessible by the processor(s) 1414.

Bus subsystem 1412 provides a mechanism for letting the various components and subsystems of computing device 1410 communicate with each other as intended. Although bus subsystem 1412 is shown schematically as a single bus, alternative implementations of the bus subsystem may use multiple busses.

Computing device 1410 can be of varying types including a workstation, server, computing cluster, blade server, server farm, or any other data processing system or computing device. Due to the ever-changing nature of computers and networks, the description of computing device 1410 depicted in FIG. 14 is intended only as a specific example for purposes of illustrating some implementations. Many other configurations of computing device 1410 are possible having more or fewer components than the computing device depicted in FIG. 14.

According to the present disclosure easily recognizable visual patterns are generated and rendered that allow for quicker and more reliable diagnosis than laborious processes of putting together several numbers to create an equivalent mental picture. The present disclosure brings together multiple factors and assures that none of the available facts are missed. It thus makes things easier for a user, lowers the mental workload and creates a useful diagnostic tool.

Effects of a treatment of a patient are directly and immediately visible and easily understandable since any changes of any measure of the pulmonary circulation in response to a certain treatment will be reflected so that the user (e.g. a caregiver or clinician) can immediately react in case of any problematic changes of the pulmonary circulation.

For instance, if a user recognizes that a certain operation of a machine used for treatment (e.g. of a ventilator) or a certain medication (e.g. given via an infusion) leads to a critical change of the patient's EDV and/or cardiac output, this will be immediately reflected in the figure-eight schematic and can thus be quickly recognized and counteracted by the user, e.g. by changing a parameter of the operation of the machine or by changing the medication.

Both, a quick diagnosis and an immediate treatment, i.e. a direct and fast interaction between diagnosis and treatment are thus possible with the present disclosure.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

According to another aspect a method and a corresponding system are presented, the method including: analyzing one or more measured physiological parameters of a patient; based on the analyzing, causing a graphical user interface to be rendered, wherein the graphical user interface includes a figure-eight schematic that represents a circulatory system of the patient, wherein: a first loop of the figure-eight schematic represents pulmonary circulation of the patient; a second loop of the figure-eight schematic represents systemic circulation of the patient; a central object that connects the first and second loops represents a heart of the patient, and each of the first and second loops includes multiple arc fragments, with each arc fragment being shaped to convey one or more of the measured physiological parameters of the patient.

The invention claimed is:

1. A method implemented using one or more processors, comprising:

analyzing one or more measured physiological parameters of a patient;

based on the analyzing, causing a graphical user interface to be rendered, wherein the graphical user interface includes a single figure-eight schematic that represents a circulatory system of the patient, the figure-eight schematic comprising two closed, continuous loop paths that directly meet and are contiguous with a single central rounded object, wherein:

a first loop of the figure-eight schematic represents pulmonary circulation of the patient;

a second loop of the figure-eight schematic represents systemic circulation of the patient;

the central object that connects the first and second loops represents a heart of the patient and is shaped to convey an end diastolic volume (EDV) of the patient, and at least a portion of the first loop is superimposed over a rendered pair of lungs, and each of the first and second loops includes multiple contiguous arc fragments, with each arc fragment being shaped to convey one or more of the measured physiological parameters of the patient, wherein cardiac output of the patient is conveyed by a length of an arc fragment of the second loop that extends from the central rounded object.

2. The method of claim 1, comprising:

rendering a first arc fragment of the first loop upstream of an arc-shaped envelope with an arc-shaped channel, with a first thickness that is selected to convey a mean pulmonary arterial pressure (MPAP) of the pulmonary circulation of the patient; and rendering a second arc fragment of the first loop downstream of the arc-shaped envelope, with a second thickness that is selected to convey pulmonary artery occlusion pressure (PAOP) of the pulmonary circulation of the patient.

3. The method of claim 1, comprising:

rendering a first arc fragment of the second loop with a third thickness that is selected to convey a mean arterial pressure (MAP) of the systemic circulation of the patient, the first arc fragment positioned upstream of an arc-shaped envelope with an arc-shaped channel; and rendering a second arc fragment of the second loop downstream of the arc-shaped envelope with a fourth thickness that is selected to convey central venous pressure (CVP) of the systemic circulation of the patient.

4. The method of claim 1, wherein a stroke volume of the patient is conveyed by a length of a secondary arc-shaped element that extends from within the arc fragment of the second loop.

5. The method of claim 1, comprising:

rendering an arc-shaped envelope with an arc-shaped channel, wherein a bore of the arc-shaped channel is sized to convey vascular resistance by constricting a thickness of a portion of the first or second loop.

6. The method of claim 1, wherein one or more of the multiple arc fragments include visual annotations of normal or baseline ranges of the respective one or more of the measured physiological parameters of the patient.

7. The method of claim 1, comprising animating the pair of lungs to demonstrate breathing of the patient.

8. The method of claim 1, comprising rendering the pair of lungs with a visual annotation that represents a level of extravascular lung water (EVLW) of the patient.

9. At least one non-transitory computer-readable medium comprising instructions that, in response to execution of the instructions by one or more processors, cause the one or more processors to perform the method of claim 1.

10. A system comprising one or more processors and memory storing instructions that, in response to execution of the instructions by the one or more processors, cause the one or more processors to:

analyze one or more measured physiological parameters of a patient;

based on the analysis, cause a graphical user interface to be rendered, wherein the graphical user interface includes a single figure-eight schematic that represents a circulatory system of the patient, the figure-eight schematic comprising two closed, continuous loop paths that directly meet and are contiguous with a single central rounded object, wherein:

a first loop of the figure-eight schematic represents pulmonary circulation of the patient;

a second loop of the figure-eight schematic represents systemic circulation of the patient;

the central object that connects the first and second loops represents a heart of the patient and is shaped to convey an end diastolic volume (EDV) of the patient, and at least a portion of the first loop is superimposed over a rendered pair of lungs, each of the first and second loops includes multiple contiguous arc fragments, with each arc fragment being shaped to convey one or more of the measured physiological parameters of the patient, wherein cardiac output of the patient is conveyed by a length of an arc fragment of the second loop that extends from the central rounded object.

11. The system of claim 10, comprising instructions to:

render a first arc fragment of the first loop upstream of an arc-shaped envelope with an arc-shaped channel with a first thickness that is selected to convey a mean pulmonary arterial pressure (MPAP) of the pulmonary circulation of the patient; and render a second arc fragment of the first loop downstream of the arc-shaped envelope with a second thickness that is selected to convey pulmonary artery occlusion pressure (PAOP) of the pulmonary circulation of the patient.

12. The system of claim 10, comprising instructions to:

render a first arc fragment of the second loop positioned upstream of an arc-shaped envelope with an arc-shaped channel with a third thickness that is selected to convey a mean arterial pressure (MAP) of the systemic circulation of the patient; and render a second arc fragment of the second loop downstream of the arc-shaped envelope with a fourth thickness that is selected to convey central venous pressure (CVP) of the systemic circulation of the patient.

\*    \*    \*    \*    \*